United States Patent
Vanderpohl, III (10) Patent No.: US 10,238,292 B2
(45) Date of Patent: Mar. 26, 2019

(54) MEASURING MULTIPLE PHYSIOLOGICAL PARAMETERS THROUGH BLIND SIGNAL PROCESSING OF VIDEO PARAMETERS

(71) Applicant: Hill-Rom Services, Inc., Batesville, IN (US)

(72) Inventor: Irvin J. Vanderpohl, III, Greenburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 739 days.

(21) Appl. No.: 14/202,567

(22) Filed: Mar. 10, 2014

(65) Prior Publication Data

US 2014/0275833 A1     Sep. 18, 2014

Related U.S. Application Data

(60) Provisional application No. 61/793,255, filed on Mar. 15, 2013.

(51) Int. Cl.
*A61B 5/00* (2006.01)
*A61B 5/16* (2006.01)
*A61G 7/002* (2006.01)
*A61G 7/05* (2006.01)

(52) U.S. Cl.
CPC .............. *A61B 5/0077* (2013.01); *A61B 5/16* (2013.01); *A61B 5/6891* (2013.01); *A61G 7/002* (2013.01); *A61G 7/05* (2013.01)

(58) Field of Classification Search
CPC .. G06K 9/624; G06K 9/00255; G06T 7/0022; G06T 7/0012; A61B 5/0205; A61B 5/02405; A61B 2576/00; A61B 5/0004; A61B 5/0077; A61B 5/02416; A61B 5/16; A61B 5/6891; A61B 5/7235; A61G 7/002; A61G 7/008; A61G 7/018; A61G 7/05; A61G 7/057
USPC .................................... 600/508, 592; 482/8
See application file for complete search history.

(56) References Cited

U.S. PATENT DOCUMENTS

| | | | |
|---|---|---|---|
| 5,524,637 | A | 6/1996 | Erickson |
| 5,860,917 | A | 1/1999 | Comanor et al. |
| 7,176,391 | B2 | 2/2007 | Metz et al. |
| 7,335,839 | B2 | 2/2008 | Metz et al. |
| 7,336,982 | B2 | 2/2008 | Yoo |

(Continued)

FOREIGN PATENT DOCUMENTS

| | | |
|---|---|---|
| EP | 2252211 A1 | 11/2010 |
| WO | 2013166341 A1 | 11/2013 |

(Continued)

OTHER PUBLICATIONS

Pépin, Jean-Louis et al. "Pulse Transit Time Improves Detection of Sleep Respiratory Events and Microarousals in Children". Clinical Investigations. Mar. 2005; 127(3):722-30.*

(Continued)

*Primary Examiner* — Thomas J Hong
*Assistant Examiner* — Helene Bor
(74) *Attorney, Agent, or Firm* — Barnes & Thornburg LLP (57) ABSTRACT

A patient support system includes a patient support apparatus, a camera, and a controller. The controller is configured to receive image data from the camera and to determine at least one of pulmonary and circulatory characteristics of a patient supported on the patient support apparatus.

20 Claims, 7 Drawing Sheets

(56) References Cited

U.S. PATENT DOCUMENTS

| | | |
|---|---|---|
| 7,437,787 B2 | 10/2008 | Bhai |
| 7,956,755 B2* | 6/2011 | Lee ................. A61B 5/4806 340/575 |
| 8,542,877 B2 | 9/2013 | Jeanne et al. |
| 8,553,940 B2 | 10/2013 | Kirenko et al. |
| 8,634,591 B2 | 1/2014 | Jeanne et al. |
| 8,666,116 B2 | 3/2014 | Kirenko et al. |
| 8,838,209 B2* | 9/2014 | Mestha ............ A61B 5/02125 600/407 |
| 2004/0103475 A1* | 6/2004 | Ogawa ................ A61B 5/16 5/613 |
| 2006/0293921 A1 | 12/2006 | McCarthy et al. |
| 2007/0085690 A1 | 4/2007 | Tran |
| 2007/0118054 A1* | 5/2007 | Pinhas ............... A61B 5/1101 600/587 |
| 2009/0318815 A1* | 12/2009 | Barnes ............... A61B 5/0062 600/473 |
| 2010/0217139 A1* | 8/2010 | Pinter ................. A61B 5/024 600/508 |
| 2011/0251493 A1* | 10/2011 | Poh ................... G06K 9/00255 600/477 |
| 2011/0286628 A1* | 11/2011 | Goncalves ....... G06F 17/30256 382/103 |
| 2011/0311119 A1 | 12/2011 | Jeanne et al. |
| 2012/0195469 A1 | 8/2012 | Kirenko et al. |
| 2012/0195486 A1 | 8/2012 | Kirenko et al. |
| 2012/0197137 A1 | 8/2012 | Jeanne et al. |
| 2013/0096439 A1 | 4/2013 | Lee et al. |
| 2013/0296660 A1 | 11/2013 | Tsien et al. |
| 2013/0331669 A1 | 12/2013 | Berte et al. |
| 2013/0345568 A1 | 12/2013 | Mestha et al. |
| 2014/0155759 A1* | 6/2014 | Kaestle .............. A61B 5/0077 600/479 |
| 2015/0105670 A1* | 4/2015 | Bresch ............... A61B 5/0077 600/479 |

FOREIGN PATENT DOCUMENTS

| | | |
|---|---|---|
| WO | 2014024104 A1 | 2/2014 |
| WO | 2014030091 A1 | 2/2014 |
| WO | 2014030439 A1 | 2/2014 |

OTHER PUBLICATIONS

Akselrod, et al., "Power Spectrum Analysis of Heart Rate Fluctuation: A Quantitative Probe of Beat-to-Beat Cardiovascular Control," Science, vol. 213, Jul. 1981, pp. 220-222.

Villa, et al., "Time Frequency Analysis of Heart Rate Variability," IEEE Trans. Biomed. Eng., vol. 16, No. 5, Sep./Oct. 1997, pp. 119-126.

Smith, et al., "Pulse Transit Time: An Appraisal of Potential Clinical Applications," Thorax, 1999, pp. 452-457.

Cardoso, "High-Order Contracts for Independent Component Analysis," Neural Comput, vol. 11, 1999, pp. 157-192.

Tarvainen, et al., "An Advanced Detrending Method with Applications to HRV Analysis," IEEE Trans. Biomed, Eng., vol. 49, No. 2, Feb. 2002, pp. 173-175.

Cardoso, "Dependence, Correlation and Gaussianity in Independent Component Analysis," Journal of Machine Learning Research 4, 2003, pp. 1177-1203.

Theis, et al., "On the Use of Joint Diagonalization in Blind Signal Processing," Circuits and Systems, 2006, pp. 1-4.

Poh, et al., "Non-Contact, Automated Cardiac Pulse Measurements Using Video Imaging and Blind Source Separation," Optics Express 18, 2010, pp. 10762-10774.

Poh, et al., "Advancements in Noncontact, Multiparameter Physiological Measurements Using a Webcam," IEEE Trans. Biomed. Eng., vol. SB, No. 1, Jan. 2011, pp. 7-11.

Comon, "Independent Component Analysis a New Concept?," Signal Process, vol. 36, 1994, pp. 287-314.

* cited by examiner

MEASURING MULTIPLE PHYSIOLOGICAL PARAMETERS THROUGH BLIND SIGNAL PROCESSING OF VIDEO PARAMETERS

This application claims the benefit, under 35 U.S.C. § 119(e), of U.S. Provisional Application No. 61/793,255, which was filed Mar. 15, 2013, and which is hereby incorporated by reference herein in its entirety.

BACKGROUND

The present disclosure is related to patient support systems. More specifically, the present disclosure is related to patient support systems including cameras.

SUMMARY

The present application discloses one or more of the features recited in the appended claims and/or the following features which, alone or in any combination, may comprise patentable subject matter:

A patient support system includes a patient support apparatus, a camera, and a controller. The controller is coupled to the patient support apparatus and to the camera.

In some embodiments, the controller may be configured to receive image data from the camera and to determine pulmonary and/or circulatory characteristics of a patient supported on the patient support apparatus. The controller may be configured to determine relative blood pressure value of a patient supported on the patient support apparatus based on image data from the camera.

In some embodiments, the controller may be configured to resolve color signals corresponding to a patient face and to a patient extremity based on image data from the camera. The controller may also be configured to determine blood volume pulse information corresponding to the patient face and to the patient extremity based on the color signal. The controller may be configured to determine a relative blood pressure value based on the blood volume pulse information corresponding to the patient face and to the patient extremity.

In some embodiments, resolving color signals corresponding to the patient face and to the patient extremity may include determining which portion of the image data contains a patient face and which portion of the image data contains a patient extremity. Determining which portion of the image data contains a patient face and which portion of the image data contains a patient extremity may include detecting skin and performing gradient analysis to detect body edges. The controller may be configured to enhance the portions of the image data that contain the patient face and the patient extremity.

In some embodiments, the controller may be configured to enhance the portions of the image data that contain the patient face and the patient extremity by blob processing the portions of the image data to reshape the image using convex hulls of contours and filling the area into a closed shape. The controller may be configured to process the closed shape using blind signal processing.

In some embodiments, determining blood volume pulse information corresponding to the patient face and to the patient extremity may include transforming the color signals into three independent source signals using independent component analysis. The independent component analysis may be based on the joint approximate diagonalization of eigenmatrices algorithm.

In some embodiments, the controller may be configured to order the three independent source signals by reviewing the power spectrum of the three independent source signals. Determining blood volume pulse information corresponding to the patient face and to the patient extremity may include selecting a signal of interest with the highest peak from the three independent source signals by determining the power spectrum of the three independent signals. The controller may be configured to smooth the signal of interest using a five-point moving average filter and bandpass filter.

In some embodiments, determining relative blood pressure based on the blood volume pulse information may include comparing time differences between peak blood volume pulse information corresponding to the patient face and peak blood volume pulse information corresponding to the patient extremity. The controller may be configured to determine actual blood pressure based on the relative blood pressure value.

In some embodiments, the camera is coupled to the patient support apparatus. In other embodiments, the camera is spaced apart from the patient support apparatus.

According to another aspect of the present disclosure, a method of determining a circulatory patient characteristic corresponding to a patient supported on a patient support apparatus is disclosed. The method may include receiving image data from a camera, determining blood volume pulse information based on the image data, and determining a relative blood pressure value based on the blood volume pulse information corresponding to the patient face and to the patient extremity.

In some embodiments, the method may include receiving an externally entered blood pressure value and determining an actual blood pressure value based on the externally entered blood pressure value and the relative blood pressure value. Determining relative blood pressure based on the blood volume pulse information may include comparing time differences between peak blood volume pulse information corresponding to a patient face and peak blood volume pulse information corresponding to a patient extremity. In some embodiments, the image data may include data corresponding to a patient face and to a patient extremity.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
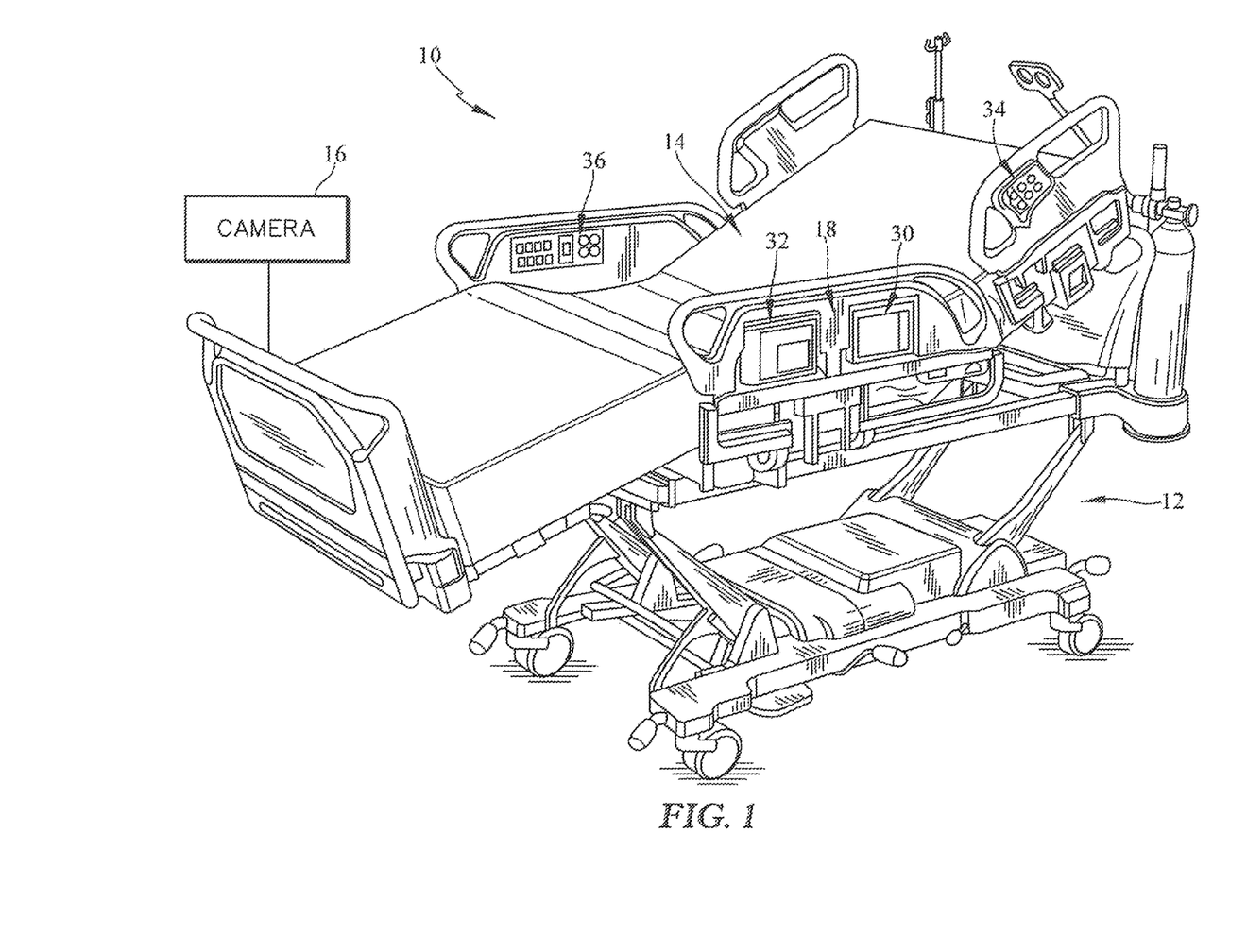
FIG. 1 is a perspective view of a patient support system including a camera.

A patient support system 10 illustratively includes a patient support apparatus (sometimes called a bed frame) 12, a support surface (sometimes called a mattress) 14, a cameral (shown diagrammatically) 16, and a control system 18 as shown in FIG. 1. The control system 18 is configured to determine physiological characteristics of a patient supported on the patient support surface 14 based on image data collected by the camera 16. The physiological information determined may then be communicated to a caregiver, used to adjust operation of the patient support system 10, or stored for other uses.

Figure 2:
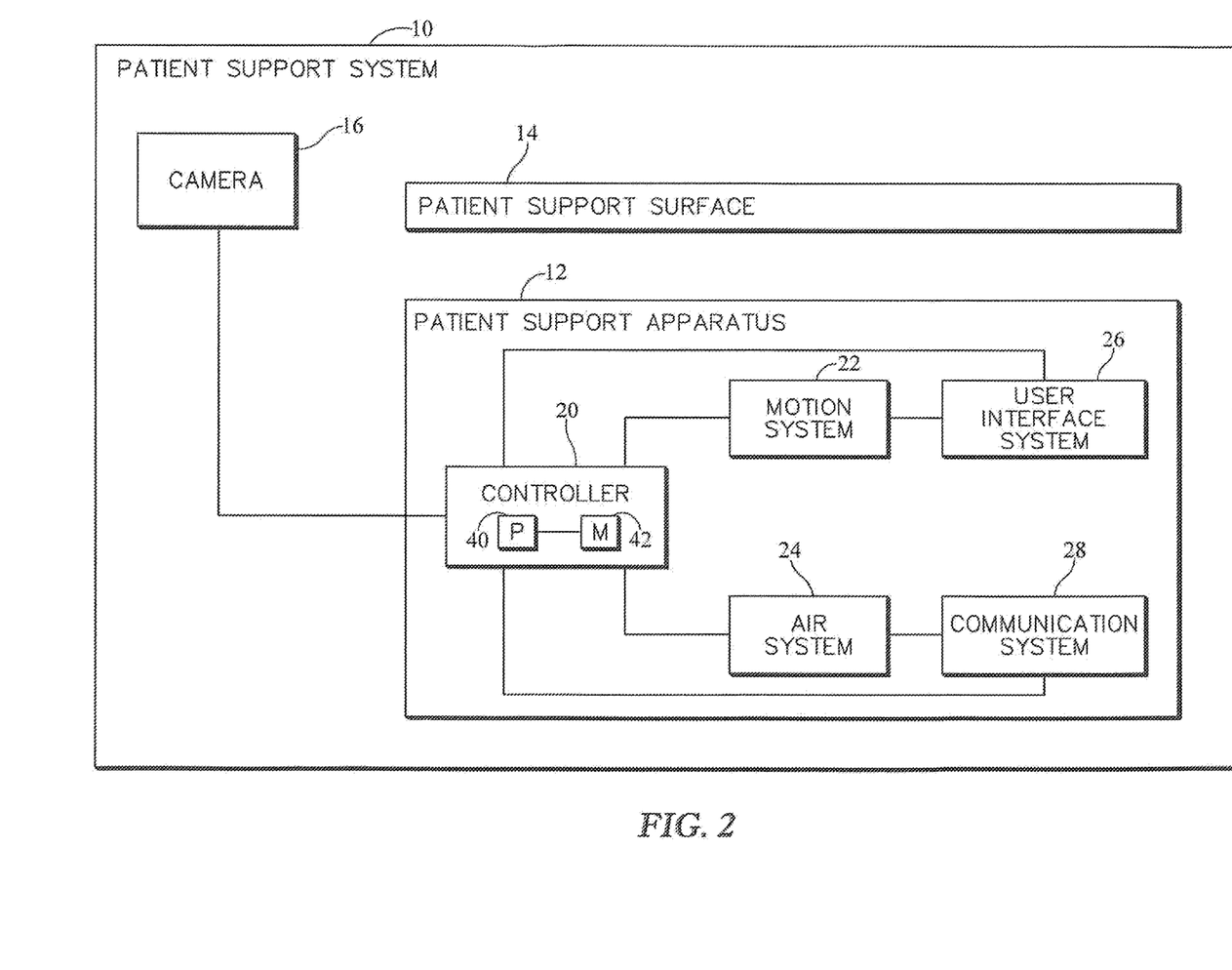
FIG. 2 is a diagrammatic view of the patient support system of FIG. 1.

In the illustrative embodiment, the control system 18 includes a controller 20, a motion system 22 coupled to the controller 20, and an air system 24 coupled to the controller 20 as shown diagrammatically in FIG. 2. The motion system 22 is configured to reposition the patient support apparatus 12 to support a patient on the patient support surface in a number of different positions (such as a sit-up position as shown in FIG. 1). The air system 24 is configured to inflate and deflate bladders in the patient support surface 14 and may provide air driven therapies to a patient on the patient support surface 14.

The control system 18 also includes a user interface system 26 coupled to the controller 20 and a communication system 28 coupled to the controller 22 as shown in FIG. 2. The user interface system 26 allows the control system to send information to a user via a touch screen display 30 and to receive information from a user via the touch screen display 30 or other user inputs 32, 34, 36 as shown in FIG. 1. The communication system 28 illustratively includes a transceiver (not shown) configured to communicate with a hospital information system, a nurse call system, and/or other networked devices in a care center.

The controller 20 illustratively includes a processor 40 and a memory 42 coupled to the processor 40. The memory 42 is configured to store instructions that are performed by the processor 40 to operate the patient support system 10.

In the illustrative embodiment, instructions stored in the memory 42 provide a method for measuring multiple physiological parameters using video images of a patient supported on the patient support system 10. By applying Independent Component Analysis (ICA), Blind Source Separation (BSS), or other Blind Signal Processing technique to the red, green and blue (RGB) components of each image frame, it is possible to extract Blood Volume Pulse (BVP) Information, which in turn can be used to quantify Heart Rate (HR), Respiratory Rate (ResR), and Heart Rate Variability (HRV), an Index for cardiac autonomic activity. Additionally, Pulse Transit Time (PTT) can be extracted and used to determine relative Blood Pressure (PB). With the Inclusion of a baseline PB reading, the method is capable of generating real time BP related data via remote monitoring. Applications for relative BP include sleep apnea detection, autonomic arousals, peripheral vascular disease, and others.

In general, Independent Component Analysis (ICA) is a technique for uncovering independent signals from a set of observations that are composed of linear mixtures of the underlying sources. Similar analysis is discussed in P Common, "Independent Component Analysis, a new concept?" Signal Process., vol. 36, pp. 287-314, 1994, which is hereby incorporated herein in its entirety to promote understanding of the present disclosure.

The underlying signal of interest in this case is the BVP that propagates through the body. During the cardiac cycle, increased flow through the body's blood vessels result in forces produced by the body onto objects that are connected or in close proximity to the body. This is the principle which allows blood pressure to be taken with a simple blood pressure cuff.

As the BPV of the patient changes, the component RGB video channels from the camera 16 records a mixture of signals with different weights. These observed signals are denoted by $y_R(t)$, $y_G(t)$, and $y_B(t)$, which are the amplitudes of the recorded signals at time point t. Assuming three underlying source signals, represented by $x_1(t)$, $x_2(t)$, and $x_3(t)$. The ICA model assumes that the observed signals are linear mixes of the sources, i.e., $$y(t)=Ax(t) \quad (1)$$

where column vectors $y(t)=[y_R(t), y_G(t), y_B(t)]$, $x(t)=[x_1(t), x_2(t), x_3(t)]^T$, and the square 3×3 matrix A contains a mixture coefficients $\alpha_{ij}$. The aim of ICA Is to find a demixing matrix W that is an approximation of the inverse of the original mixing matrix A whose output $$\hat{x}(t)=Wy(t) \quad (2)$$

Is an estimate of the vector x(t) containing the underlying source signals. To uncover the independent sources, W must maximize the non-Gaussianity of each source. In practice, Iterative methods are used to maximize or minimize a given cost function that measures non-Gaussianity.

Figure 3:
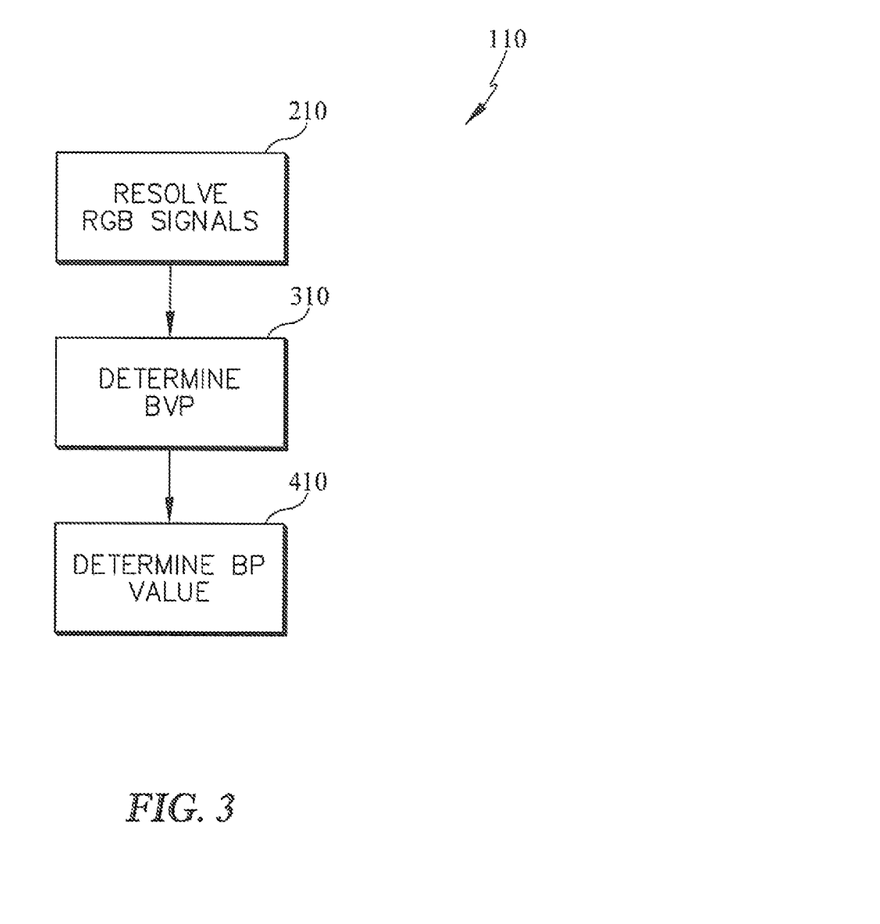
FIG. 3 is a flow chart showing a process for determining a blood pressure value based on image data from the camera.

In the illustrative embodiment, the memory 42 includes instructions for performing a process 110 to provide relative and/or actual blood pressure values based on information from the camera 16 as shown in FIGS. 3-6. The process 110 includes the sub-processes of resolving RGB signals 210, determining BVP 310, and finally determining a BP Value 410 as shown in FIG. 3.

Figure 4:
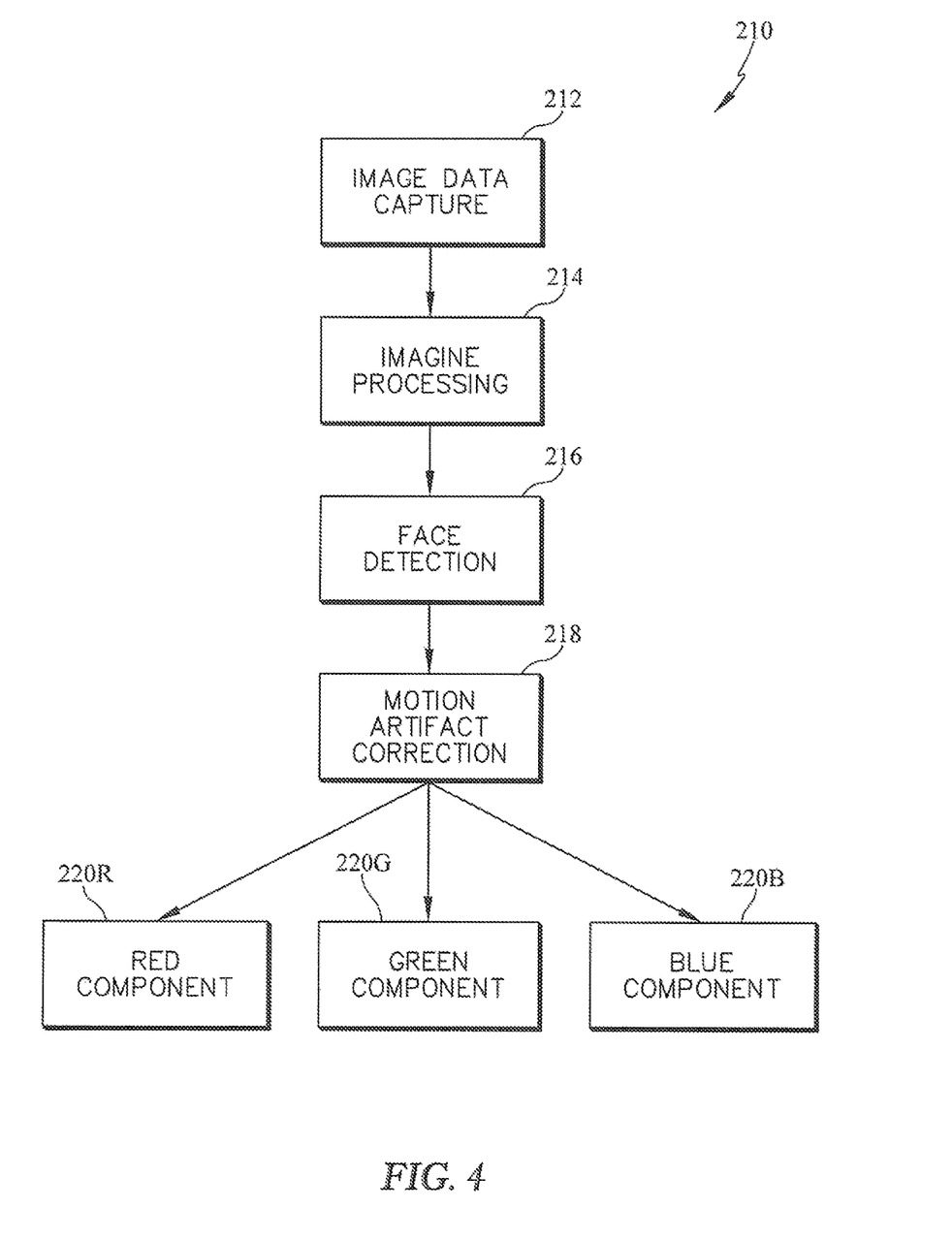
FIG. 4 is a flow chart showing a first sub-process included in the process of FIG. 3.

Turning now to FIG. 4, the subprocess 210 is shown. In a first step 212 of process 210, the camera 16 is used to capture image data. The image data is illustratively captured 15 fps (frames per second), which is adequate for recovery of BVP. The image data is first preprocessed in a step 214 to correct for any lighting or color problems. The image is then analyzed to determine which portion on the Image contains the face, hands, and feet in a step 216. The face portion is needed to capture any of the physiological parameters discussed, while a hand or foot extremity is needed to capture relative Blood Pressure. The face, hands, and feet components of the image are determined through a segmentation process that uses skin detection coupled with gradient analysis to detect body edges. Proper identification of each component can be made using the known anatomy of the human body to infer which skin positions are face, hands, and feet. Image artifacts that are smaller than a predetermined limit (i.e. 300 pixels) are discarded.

Once the contour of the components are known, blob processing will further enhance the portion of the Image of Interest by reshaping the image using convex hulls of contours and filling the area into a closed shape. This shape represents the area of interest for the Blind Signal Processing. The data is then further preprocessed in steps 218R, 218G, 218B to remove offset and gain errors and trending artifacts (smoothing). This results in an 8-bit signal for each RGB signal.

Detrending, if necessary, would be accomplished through normalization based on a smoothness priors approach and normalized as follows:

$$y'_i(t) = \frac{y_i(t) - \mu_i}{\sigma_i} \quad (3)$$

for each i=1, 2, 3 where and σ are the mean and standard deviation of y$_i$(t), respectively. A similar approach is discussed in M. P. Tarvainen, P. O. Ranta-Aho, and P. A. Karjalainin, "An advanced detrending method with applications to HRV analysis," IEEE Trans. Blamed. Eng., vol. 49, no. 2, pp 173-175, February 2002, which is hereby incorporated herein in its entirety to promote understanding of the present disclosure.

Figure 5:
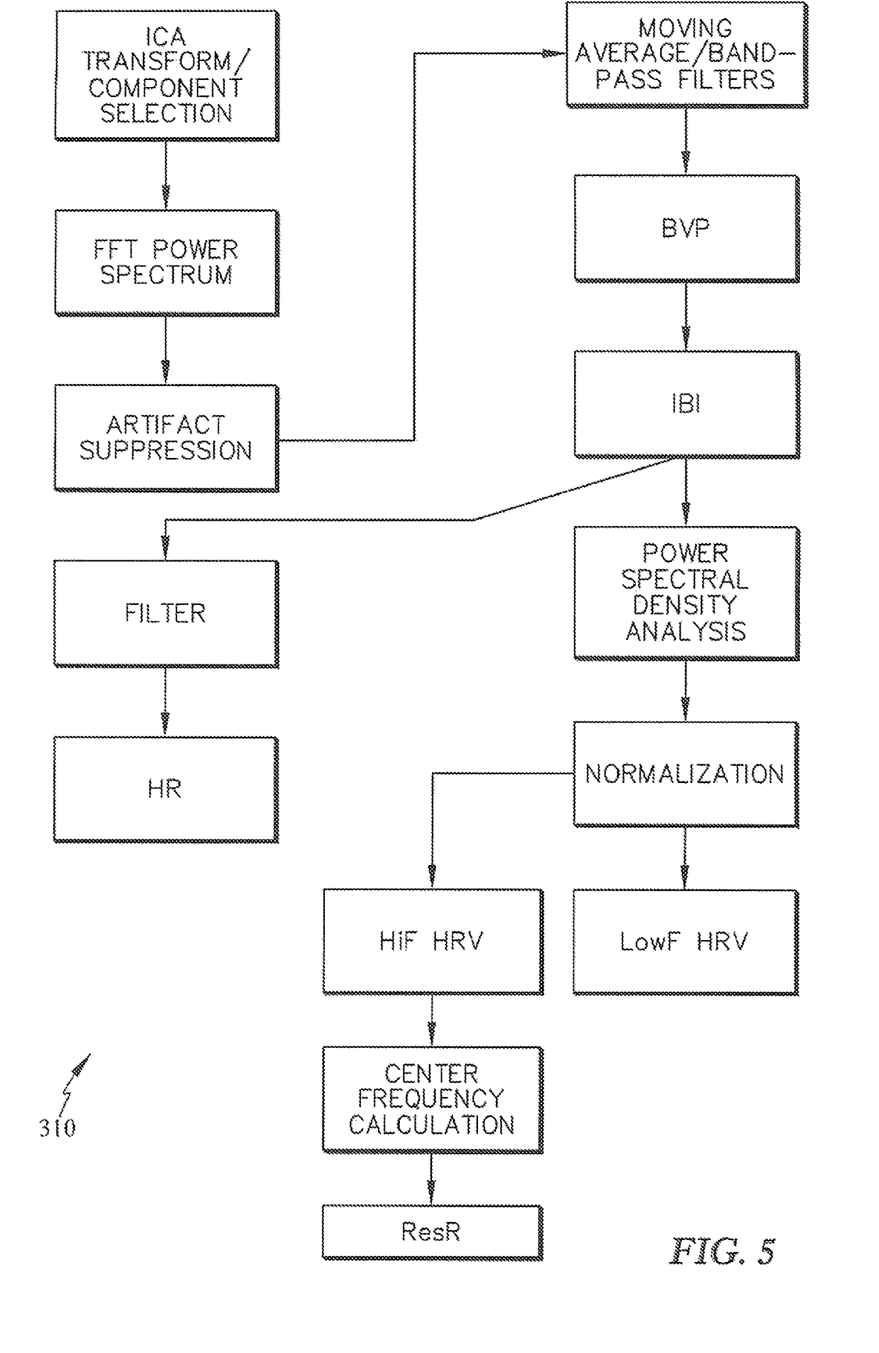
FIG. 5 is a flow chart showing a second sub-process included in the process of FIG. 3.

Turning now to FIG. 5, the subprocess 310 for determining BVP is shown. The normalized raw data are decomposed into 3 independent source signals using ICA based on the Joint Approximate Diagonalization of Eigenmatrices (JADE) algorithm. Similar processes/algorithms are discussed in J: F. Cardoso, "High-order contrasts for independent component analysis," Neural Comput., vol. 11, pp. 157-192, 1999, which is hereby incorporated herein in its entirety to promote understanding of the present disclosure. ICA is able to separate fluctuations caused predominately by the BVP from the observed raw signals.

Once the ICA signals are generated, the function responsible for BVP must be uncovered. This algorithm will generate three independent signals, in random order, that must be further analyzed. This is accomplished by reviewing the power spectrum of the signals and selecting the one with the highest peak. Refining the analysis further includes selecting the signal with a peak in the range where BVP is known to exist and using the raw weight value to ensure that a patient is indeed present in the bed. Fortunately, the algorithm will generally result in the signal of interest being found in the same position (i.e. the 2$^{nd}$ of the 3 generated signals).

Once the signal of interest is identified, signal is smoothed using a five-point moving average filter and bandpass filtered in the area of interest (0.7-4.0 Hz). To refine the BVP peak fiducial point, the signal is interpolated with a cubic spline function at a frequency of 256 Hz. From the resulting function the Interbeat Interval (IBI) can be determined. To further remove artifacts such as ectropoc beats or motion, the IBI signal is filtered using the noncausal of variable threshold (NC-VT) algorithm. A similar algorithm is described in "J. Vila, F. Palaclos, J. Presedo, M. Fernandez-Delgato, P. Felix, and S. Barrow, "Time frequency analysis of heart rate variability," IEEE Trans. Blamed. Eng vol. 16, no. 5, pp 119-126, September/Octobter 1997, which is incorporated herein by reference in its entirety to promote understanding of the present disclosure. Heart Rate can then be calculated from the mean IBI time series as 60/IBI.

Analysis of HRV can then be performed by power spectral density estimation using the Lomb periodogram. The low frequency (LowF) (0.04-0.15 Hz) component is modulated by baroflex activity and includes both sympathetic and parasympathetic influences. Such analyses are discussed in A S. Akselrod, D. Gordon, F. A, Ubel, D. C. Shannon, A. C. Berger, and R. J. Cohen, "Power spectrum analysis of heart rate fluctuation: A quantitative probe of beat-to-beat cardiovascular control," Science, vol. 213, pp. 220-222, July 1981, which is hereby incorporated herein in its entirety to promote understanding of the present disclosure. The high frequency (HiF) (0.15-0.40 Hz) component reflects parasympathetic influence on the heart through efferent vagal activity and is connected to Respiratory Sinus Arrhythmia (RSA), a cardiorespiratory phenomenon characterized by IBI fluctuations that are in phase with inhalation and exhalation. The ratio of LowF/HiF is considered to mirror sympatho/vagal balance or to reflect sympathetic modulations.

Since the HiF component is connected to breathing, the Respiratory Rate can be estimated from the HRV power spectrum, when the frequency of respiration changes, the center frequency of the HiF peak shifts in accordance to ResR. Then a breathing rate 325 can calculated as 60/f$_{HiF-peak}$.

Figure 6:
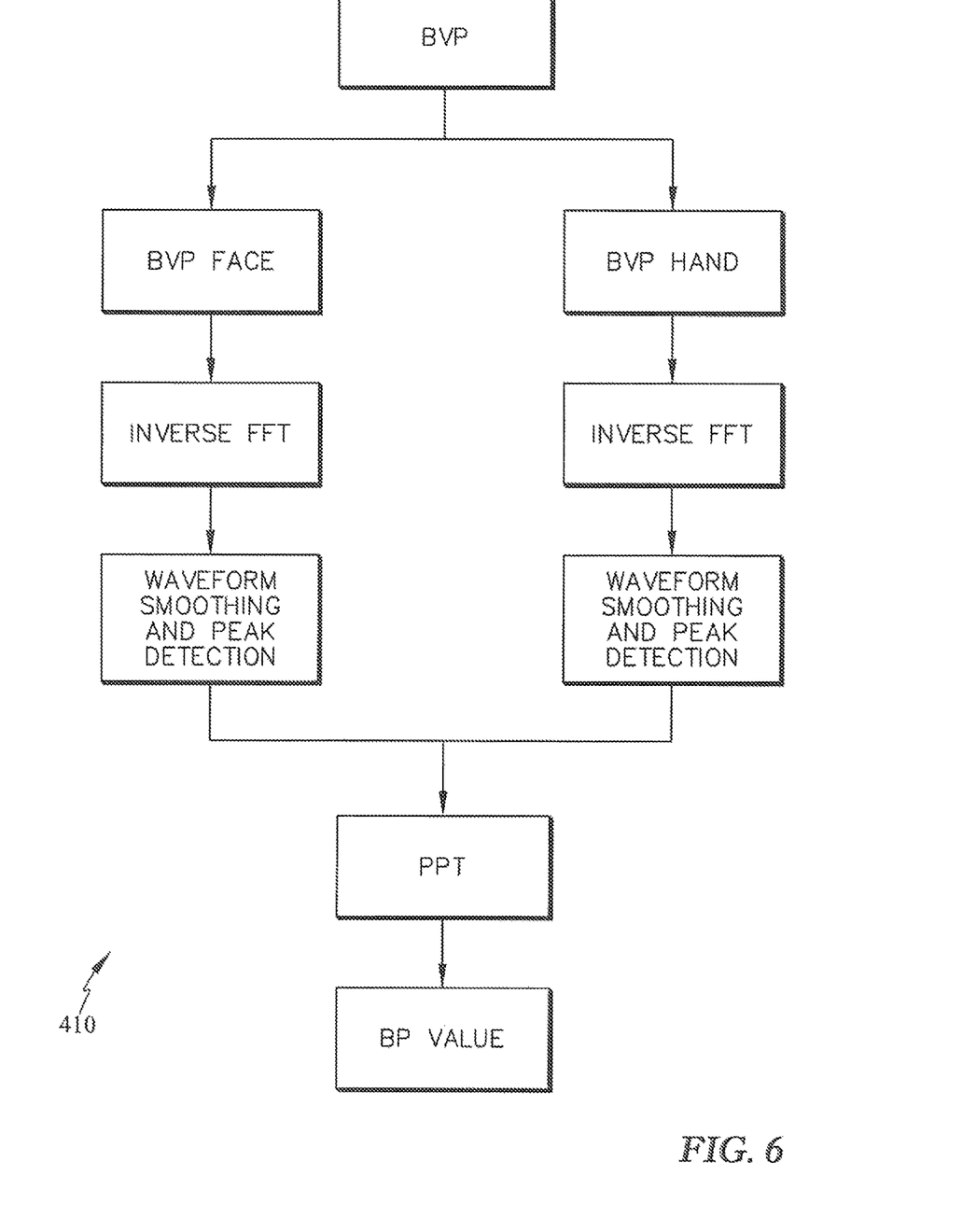
FIG. 6 is a flow chart showing a third sub-process included in the process of FIG. 3.

Relative BP can be obtained from the time difference between peak BPV at different points in the body as suggested in the sub-process 410 shown in FIG. 6. PTT is a measure of the time taken for the arterial pulse pressure wave to travel from the aortic valve to a peripheral site. Pulse transit time is inversely proportional to blood pressure, as increasing vessel wall stiffness at a higher blood pressure increases the pulse wave velocity, and hence reduces the pulse transit time. A discussion of pulse transit time can be found in W R. Smith, J, Argod, J. Pepin, P. Levy, "Pulse transit time: an appraisal of potential clinical application", Thorax, vol. 54, pp. 452-458, 1999, which is hereby incorporated herein in its entirety to promote understanding of the present disclosure.

The relative BP value is a key indicator of the arousal state of the patient and can be an indicator of stress or an impending adverse event where hypertension is an indicator. PTT can be used to indicate a rapid change in real-time blood pressure which can trigger the control system 18 to trigger an alarm or change operational characteristics of the patient support system 10. The actual correlation of PTT to blood pressure can be determined via a simple monotonic relationship between the two. Inclusion of a baseline PB reading, manually entered, taken from the EMR, or taken from a dedicated measuring device, may be employed to assist in this effort.

Interesting applications also exist in the combining of the relative PB data with the previously described HR data. For example, in addition to changes in PTT, heart rate rises during apnea and rises further at apnea termination. These heart rate changes, which reflect alterations in sympathetic function, may be useful in identifying autonomic arousals. Indication of peripheral vascular disease may also be possible, as may be cardiac complications in children and infants.

Good correlation may be achieved using the described patient support system 10 to determine patient characteristics when compared to standard measurement devices. Specifically comparisons have resulted in a standard deviation for HR of 0.83 bpm and 1.33 beats/min for ResR. Video data frames are sampled at a rate of 15 Hz.

Figure 7:
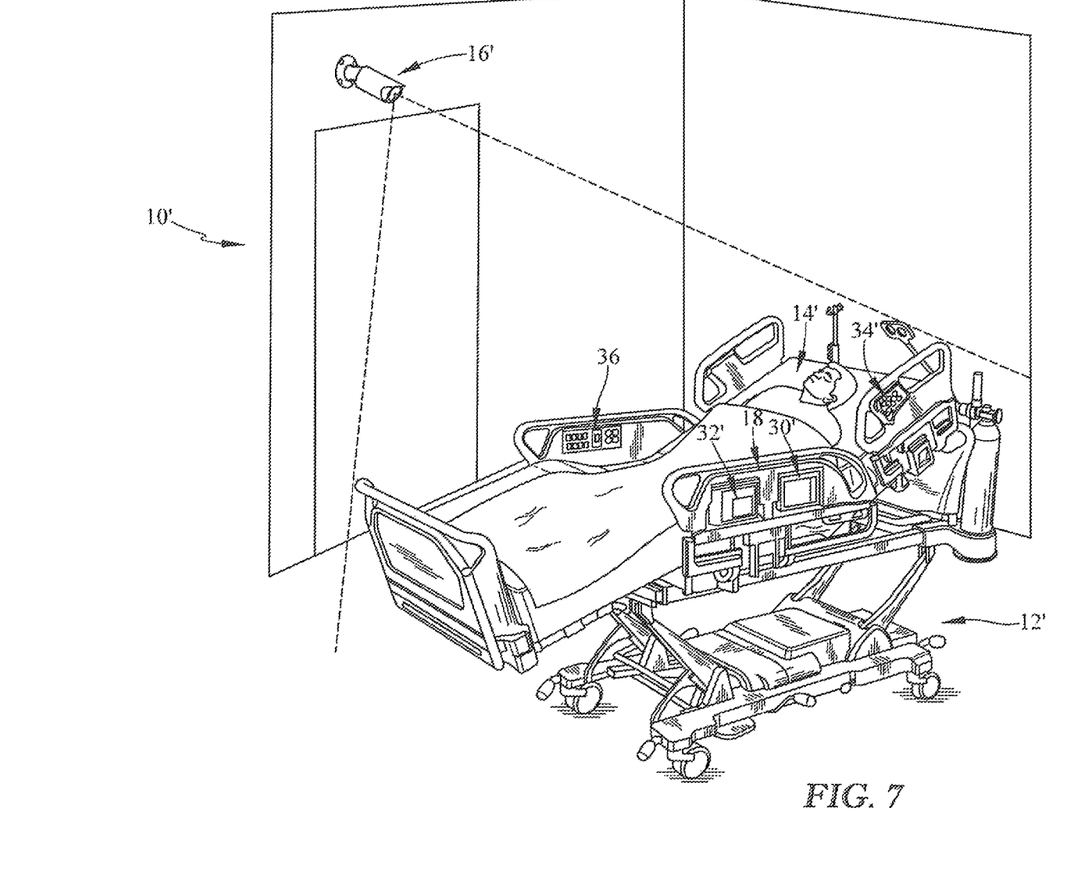
FIG. 7 is a perspective view of an alternative patient support system.

In an alternative embodiment, a camera 16' may be spaced apart from a patient support apparatus 12' and the patient support surface 14' but may still comprise part of the patient support system 10' as shown in FIG. 7. Patient support system 10' is substantially similar to patient support system 10 except as shown and described. In such embodiments, the camera 16' is coupled to the controller 20' via the communication system 28'. Discussion of using a remote camera is included in M Poh, D. McDuff, R. Picard, "Advancements in Noncontact, Multiparameter Physiological Measurements Using a Webcam", IEEE Trans. Blamed. Eng., vol. 58, No. 1, pp 7-11, January 2011, which is hereby incorporated herein in its entirety to promote understanding of the present disclosure.

Although certain illustrative embodiments have been described in detail above, variations and modifications exist within the scope and spirit of this disclosure as described and as defined in the following claims.

The invention claimed is:

1. A patient support system comprising
a patient support apparatus embodied as a patient bed having a touch screen display and user inputs spaced from the touch screen display,
a camera, and
a controller coupled to the patient support apparatus and to the camera, the controller also being coupled to the touch screen display and to the user inputs, the controller configured to receive image data from the camera and to use blind signal processing image analysis to determine at least one of pulmonary and circulatory characteristics of a patient supported on the patient support apparatus and to determine a pulse transit time (PTT) of an amount of time taken for an arterial pulse pressure wave to travel from the patient's aortic valve to a peripheral site, wherein the controller is also operable to control a motion system that is operable to reposition a patient supported on the patient bed and an air system that is operable to inflate and deflate at least one bladder of a mattress of the patient bed, wherein the PTT is used to trigger a change in operational characteristics of the patient support apparatus, wherein the change in the operational characteristics includes repositioning the patient using the motion system and changing inflation of the at least one bladder using the air system.

2. The patient support system of claim 1, wherein the controller is configured to determine relative blood pressure value of a patient supported on the patient support apparatus based on image data from the camera.

3. The patient support system of claim 2, wherein the controller is configured to resolve color signals corresponding to a patient face and to a patient extremity based on image data from the camera, to determine blood volume pulse information corresponding to the patient face and to the patient extremity based on the color signal, and to determine a relative blood pressure value based on the blood volume pulse information corresponding to the patient face and to the patient extremity.

4. The patient support system of claim 3, wherein resolving color signals corresponding to the patient face and to the patient extremity includes determining which portion of the image data contains a patient face and which portion of the image data contains a patient extremity.

5. The patient support system of claim 4, wherein determining which portion of the image data contains a patient face and which portion of the image data contains a patient extremity includes detecting skin and performing gradient analysis to detect body edges.

6. The patient support system of claim 4, wherein the controller is configured to enhance the portions of the image data that contain the patient face and the patient extremity.

7. The patient support system of claim 6, wherein the controller is configured to enhance the portions of the image data that contain the patient face and the patient extremity by blob processing the portions of the image data to reshape the image using convex hulls of contours and filling the area into a closed shape.

8. The patient support system of claim 7, wherein the controller is configured to process the closed shape.

9. The patient support system of claim 3, wherein determining blood volume pulse information corresponding to the patient face and to the patient extremity includes transforming the color signals into three independent source signals using independent component analysis.

10. The patient support system of claim 9, wherein the independent component analysis is based on the joint approximate diagonalization of eigenmatrices algorithm.

11. The patient support system of claim 9, wherein the controller is configured to order the three independent source signals by reviewing the power spectrum of the three independent source signals.

12. The patient support system of claim 11, wherein determining blood volume pulse information corresponding to the patient face and to the patient extremity includes selecting a signal of interest with the highest peak from the three independent source signals by determining the power spectrum of the three independent signals.

13. The patient support system of claim 12, wherein controller is configured to smooth the signal of interest using a five-point moving average filter and bandpass filter.

14. The patient support surface of claim 2, wherein determining relative blood pressure based on the blood volume pulse information includes comparing time differences between peak blood volume pulse information corresponding to the patient face and peak blood volume pulse information corresponding to the patient extremity.

15. The patient support surface of claim 2, wherein the controller is configured to determine actual blood pressure based on the relative blood pressure value.

16. The patient support system of claim 1, wherein the camera is coupled to the patient support apparatus.

17. A method of determining a circulatory patient characteristic corresponding to a patient supported on a patient support apparatus, the method comprising
receiving image data from a camera,
determining a pulse transit time (PTT) of an amount of time taken for an arterial pulse pressure wave to travel from the patient's aortic valve to a peripheral site and determining blood volume pulse information based on the image data using a controller of the patient support apparatus to perform blind signal processing image analysis, wherein the patient support apparatus is embodied as a patient bed having a touch screen display and user inputs spaced from the touch screen display, the controller being coupled to the touch screen display and to the user inputs, wherein the controller is also operable to control a motion system that is operable to reposition a patient supported on the patient bed and an air system that is operable to inflate and deflate at least one bladder of a mattress of the patient bed,
determining with the controller a relative blood pressure value based on the blood volume pulse information corresponding to a face of the patient and to an extremity of the patient, and
using the PTT to trigger a change in operational characteristics of the patient support apparatus, wherein the change in the operational characteristics includes repositioning the patient using the motion system and changing inflation of the at least one bladder using the air system.

18. The method of claim 17, further comprising receiving an externally entered blood pressure value and determining an actual blood pressure value based on the externally entered blood pressure value and the relative blood pressure value.

19. The method of claim 17, wherein determining relative blood pressure based on the blood volume pulse information includes comparing time differences between peak blood volume pulse information corresponding to the face of the patient and peak blood volume pulse information corresponding to the extremity of the patient.

20. The method of claim 17, further comprising determining which portion of the image data includes data corresponding to the face of the patient and which portion of the image data contains data corresponding to the extremity of the patient.

* * * * *

UNITED STATES PATENT AND TRADEMARK OFFICE
CERTIFICATE OF CORRECTION

PATENT NO.       : 10,238,292 B2
APPLICATION NO.  : 14/202567
DATED            : March 26, 2019
INVENTOR(S)      : Irvin J. Vanderpohl, III Page 1 of 1

It is certified that error appears in the above-identified patent and that said Letters Patent is hereby corrected as shown below:

On the Title Page

Item (72) Inventor, replace the word "Greenburg" with --Greensburg--.

In the Claims

In Claim 14, Column 8, Line 19, replace the word "surface" with --system--.

In Claim 15, Column 8, Line 25, replace the word "surface" with --system--.

Signed and Sealed this
Fourteenth Day of May, 2019

Andrei Iancu
*Director of the United States Patent and Trademark Office*